(12) United States Patent  
Leedle

(10) Patent No.: US 9,737,305 B2  
(45) Date of Patent: Aug. 22, 2017

(54) VASCULAR DEVICE AND METHOD FOR VALVE LEAFLET APPOSITION

(71) Applicant: Rex Medical, L.P., Conshohocken, PA (US)

(72) Inventor: John D. Leedle, Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 14/922,062

(22) Filed: Oct. 23, 2015

(65) Prior Publication Data

US 2016/0038146 A1    Feb. 11, 2016

Related U.S. Application Data

(62) Division of application No. 13/783,246, filed on Mar. 2, 2013, now Pat. No. 9,168,122.

(Continued)

(51) Int. Cl.
*A61F 2/06* (2013.01)
*A61B 17/12* (2006.01)
(Continued)

(52) U.S. Cl.
CPC .......... *A61B 17/12* (2013.01); *A61B 17/0644* (2013.01); *A61B 17/12036* (2013.01);
(Continued)

(58) Field of Classification Search
CPC ...... A61F 2002/075; A61F 2/89; A61F 2/848; A61F 2/07; A61B 17/0644; A61B 17/12109; A61B 17/12172
See application file for complete search history.

(56) References Cited

U.S. PATENT DOCUMENTS

| | | |
|---|---|---|
| 4,275,469 A | 6/1981 | Gabbay |
| 4,759,758 A | 7/1988 | Gabbay |

(Continued)

FOREIGN PATENT DOCUMENTS

| | | |
|---|---|---|
| DE | 19/857887 | 7/2000 |
| EP | 1894543 | 3/2008 |

(Continued)

OTHER PUBLICATIONS

European Search Report dated Aug. 8, 2013 for European Patent Application No. 13164268.8.

(Continued)

*Primary Examiner* — Thomas J Sweet
*Assistant Examiner* — Tiffany Shipmon
(74) *Attorney, Agent, or Firm* — Neil D. Gershon

(57) ABSTRACT

A vascular device having a plurality of struts having a distal portion and a proximal portion. The distal portion of the struts are retained in a converged position. The struts diverge radially outwardly. A plurality of vessel penetrating members extend from the proximal portion of the struts for engaging the internal wall of the vessel, wherein release of the retention of the distal portions of the struts causes the distal portions to move outwardly away from the longitudinal axis and the proximal portions of the struts to move inwardly toward the longitudinal axis such that the vessel engaging members pull the internal wall of the vessel radially inwardly.

18 Claims, 3 Drawing Sheets

Related U.S. Application Data

(60) Provisional application No. 61/638,643, filed on Apr. 26, 2012.

(51) Int. Cl.
*A61F 2/24* (2006.01)
*A61B 17/064* (2006.01)
*A61B 17/00* (2006.01)

(52) U.S. Cl.
CPC .. *A61B 17/12109* (2013.01); *A61B 17/12172* (2013.01); *A61F 2/06* (2013.01); *A61F 2/2445* (2013.01); *A61F 2/2475* (2013.01); *A61B 2017/00783* (2013.01); *A61B 2017/0641* (2013.01); *A61B 2017/12054* (2013.01); *A61F 2220/0016* (2013.01); *A61F 2230/0008* (2013.01); *A61F 2230/0067* (2013.01)

(56) References Cited

U.S. PATENT DOCUMENTS

| | | |
|---|---|---|
| 5,019,102 A | 5/1991 | Hoene |
| 5,147,389 A | 9/1992 | Lane |
| 5,151,105 A | 9/1992 | Kwan-Gett |
| 5,258,022 A | 11/1993 | Davidson |
| 5,350,398 A | 9/1994 | Pavcnik et al. |
| 5,358,518 A | 10/1994 | Camilli |
| 5,375,612 A | 12/1994 | Cottenceau et al. |
| 5,395,390 A | 3/1995 | Simon et al. |
| 5,397,351 A | 3/1995 | Pavcnik et al. |
| 5,397,355 A | 3/1995 | Marin |
| 5,411,552 A | 5/1995 | Anderson |
| 5,443,500 A | 8/1995 | Sigwart |
| 5,500,014 A | 3/1996 | Quijano et al. |
| 5,540,712 A | 7/1996 | Kleshinski et al. |
| 5,545,210 A | 8/1996 | Hess et al. |
| 5,562,728 A | 10/1996 | Lazarus |
| 5,591,197 A | 1/1997 | Orth |
| 5,593,417 A | 1/1997 | Rhodes |
| 5,609,598 A | 3/1997 | Laufer |
| 5,643,278 A | 7/1997 | Wijay |
| 5,674,279 A | 10/1997 | Wright |
| 5,746,766 A | 5/1998 | Edoga |
| 5,792,155 A | 8/1998 | Van Cleef |
| 5,800,526 A | 9/1998 | Anderson et al. |
| 5,810,847 A | 9/1998 | Laufer et al. |
| 5,827,322 A | 10/1998 | Williams |
| 5,843,164 A | 12/1998 | Frantzen et al. |
| 5,855,601 A | 1/1999 | Bessler et al. |
| 5,876,434 A | 3/1999 | Flomenblit et al. |
| 5,885,258 A | 3/1999 | Sachdeva et al. |
| 5,902,317 A | 5/1999 | Kleshinski et al. |
| 5,957,949 A | 9/1999 | Leonhardt et al. |
| 6,004,347 A | 12/1999 | McNamara et al. |
| 6,004,348 A | 12/1999 | Banas et al. |
| 6,014,589 A | 1/2000 | Farley et al. |
| 6,027,525 A | 2/2000 | Suh et al. |
| 6,033,398 A | 3/2000 | Farley et al. |
| 6,036,687 A | 3/2000 | Laufer et al. |
| 6,042,606 A | 3/2000 | Frantzen |
| 6,053,896 A | 4/2000 | Wilson et al. |
| 6,071,277 A | 6/2000 | Farley et al. |
| 6,080,160 A | 6/2000 | Chen et al. |
| 6,086,610 A | 7/2000 | Duerig et al. |
| 6,113,612 A | 9/2000 | Swanson et al. |
| 6,120,534 A | 9/2000 | Ruiz |
| 6,129,758 A | 10/2000 | Love |
| 6,136,025 A | 10/2000 | Barbut et al. |
| 6,139,536 A | 10/2000 | Mikus et al. |
| 6,149,660 A | 11/2000 | Laufer et al. |
| 6,162,245 A | 12/2000 | Jayaraman |
| 6,179,878 B1 | 1/2001 | Duerig et al. |
| 6,200,336 B1 | 3/2001 | Pavcnik et al. |
| 6,221,102 B1 | 4/2001 | Baker et al. |
| 6,224,626 B1 | 5/2001 | Steinke |
| 6,231,561 B1 | 5/2001 | Frazier et al. |
| 6,254,564 B1 | 7/2001 | Wilk et al. |
| 6,258,118 B1 | 7/2001 | Baum et al. |
| 6,287,339 B1 | 9/2001 | Vazquez et al. |
| 6,290,721 B1 | 9/2001 | Heath |
| 6,299,636 B1 | 10/2001 | Schmitt et al. |
| 6,299,637 B1 | 10/2001 | Shaolian et al. |
| 6,302,917 B1 | 10/2001 | Dua et al. |
| 6,309,416 B1 | 10/2001 | Swanson et al. |
| 6,425,915 B1 | 7/2002 | Khosravi et al. |
| 6,440,163 B1 | 8/2002 | Swanson et al. |
| 6,454,799 B1 | 9/2002 | Schreck |
| 6,503,272 B2 | 1/2003 | Duerig et al. |
| 6,511,491 B2 | 1/2003 | Grudem et al. |
| 6,527,800 B1 | 3/2003 | McGuckin et al. |
| 6,572,646 B1 | 6/2003 | Boylan et al. |
| 6,582,461 B1 | 6/2003 | Burmeister et al. |
| 6,626,899 B2 | 9/2003 | Houser et al. |
| 6,635,080 B1 | 10/2003 | Lauterjung et al. |
| 6,695,878 B2 | 2/2004 | McGuckin et al. |
| 6,733,525 B2 | 5/2004 | Yang et al. |
| 6,740,111 B1 | 5/2004 | Lauterjung |
| 7,007,698 B2 | 3/2006 | Thornton |
| 7,041,128 B2 | 5/2006 | McGuckin et al. |
| 8,109,990 B2 | 2/2012 | Paul et al. |
| 8,348,997 B2 | 1/2013 | Thompson et al. |
| 2001/0005787 A1 | 6/2001 | Oz et al. |
| 2001/0039432 A1* | 11/2001 | Whitcher .......... A61F 2/01 606/200 |
| 2002/0002401 A1 | 1/2002 | McGuckin et al. |
| 2002/0032481 A1 | 3/2002 | Gabbay |
| 2002/0055772 A1 | 5/2002 | McGuckin et al. |
| 2002/0138129 A1 | 9/2002 | Armstrong et al. |
| 2003/0018294 A1 | 1/2003 | Cox |
| 2003/0199987 A1 | 10/2003 | Berg et al. |
| 2004/0098098 A1 | 5/2004 | McGuckin, Jr. et al. |
| 2004/0220593 A1 | 11/2004 | Greenhalgh |
| 2005/0049692 A1 | 3/2005 | Numamoto et al. |
| 2006/0122692 A1 | 6/2006 | Gilad et al. |
| 2006/0149360 A1 | 7/2006 | Schwammenthal et al. |
| 2006/0190074 A1 | 8/2006 | Hill et al. |
| 2007/0112423 A1 | 5/2007 | Chu |
| 2007/0185571 A1 | 8/2007 | Kapadia et al. |
| 2008/0221669 A1 | 9/2008 | Camilli et al. |
| 2008/0294189 A1 | 11/2008 | Moll et al. |
| 2011/0202127 A1* | 8/2011 | Mauch .......... A61F 2/2445 623/2.11 |

FOREIGN PATENT DOCUMENTS

| | | |
|---|---|---|
| WO | WO/9740755 | 11/1997 |
| WO | WO/9819629 | 5/1998 |
| WO | WO/9956655 | 11/1999 |
| WO | WO/0128459 | 4/2001 |
| WO | 01/49213 | 7/2001 |
| WO | WO02/100297 | 12/2002 |
| WO | 2006/004679 | 1/2006 |
| WO | WO/2007/061927 | 5/2007 |
| WO | WO2007/067942 | 6/2007 |
| WO | WO/2008/100382 | 8/2008 |
| WO | WO/2010/017085 | 2/2010 |
| WO | WO/2010/098940 | 9/2010 |

OTHER PUBLICATIONS

European Search Report dated Aug. 4, 2015 for European Patent Application No. 15158728.4.

* cited by examiner

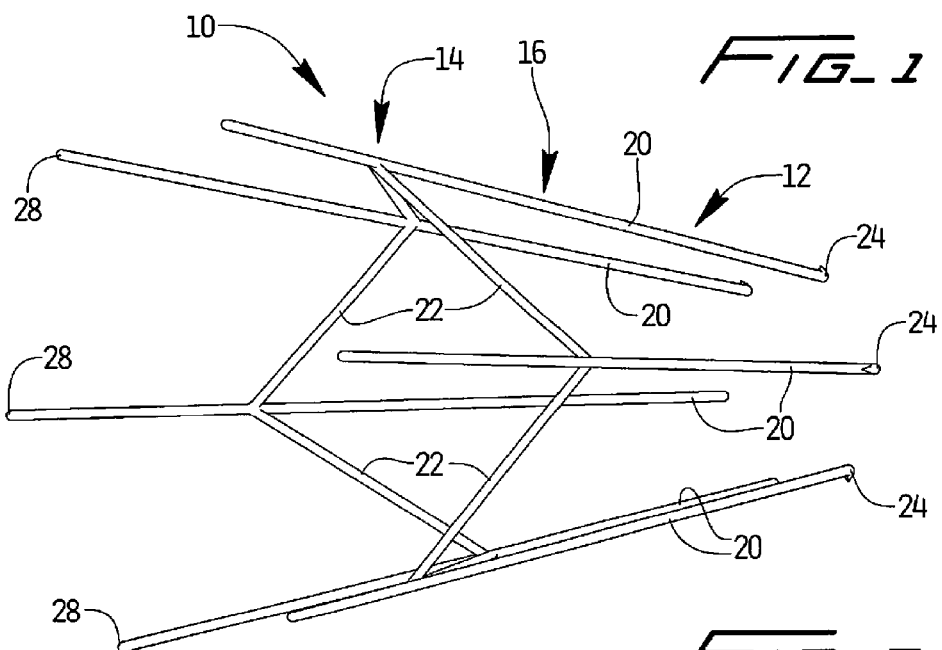
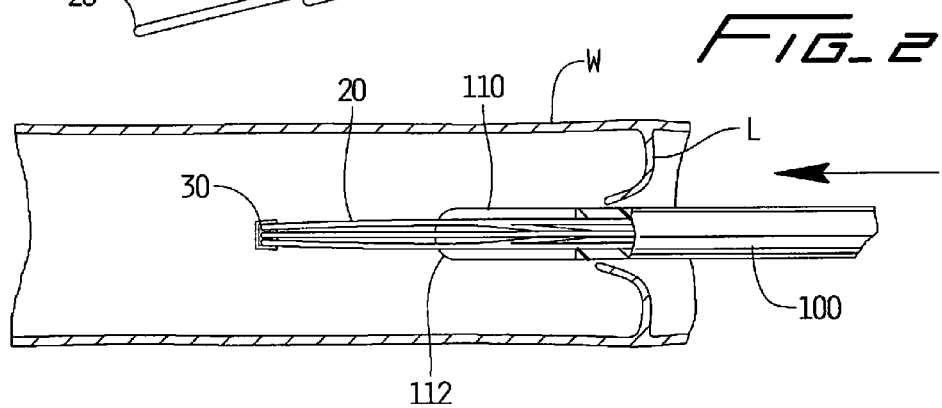
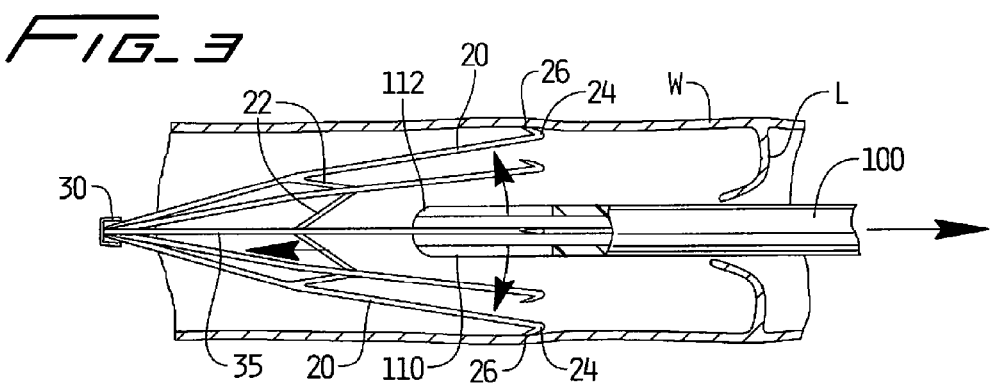

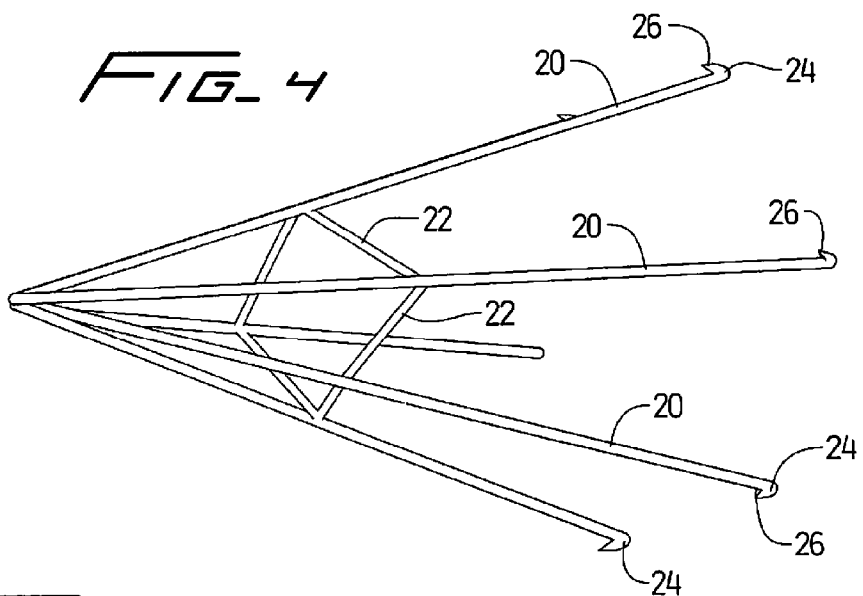
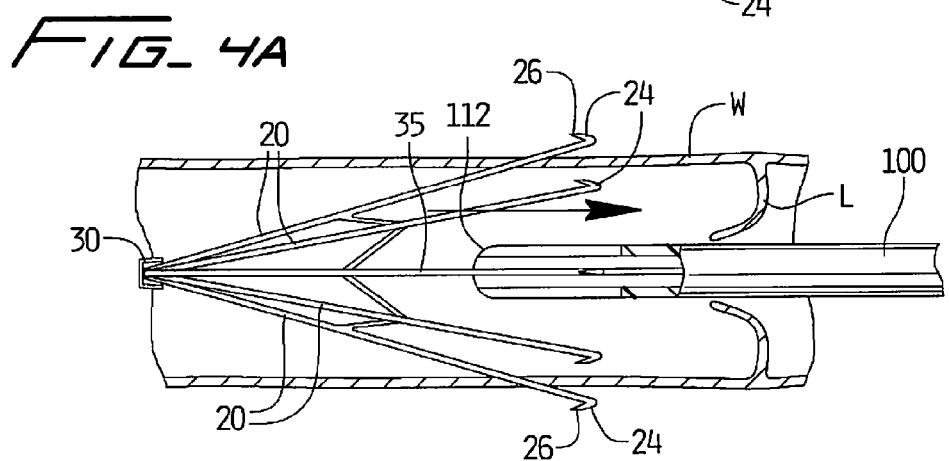
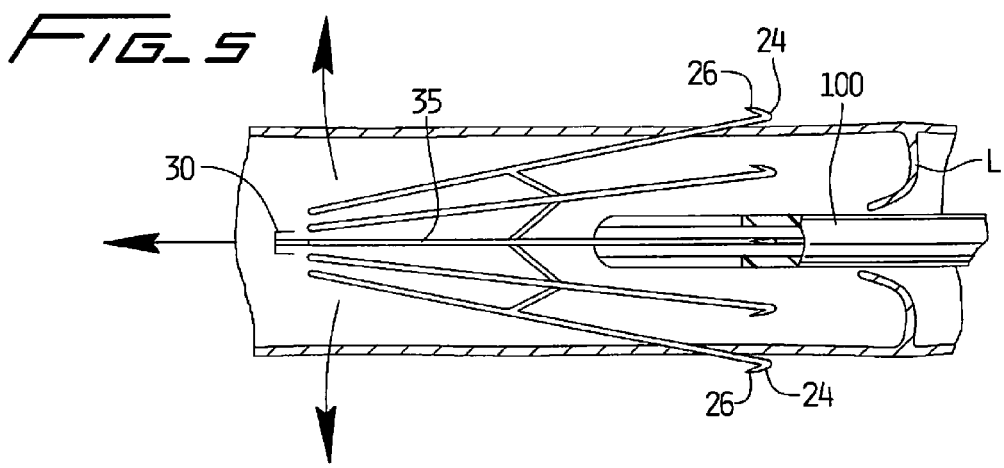

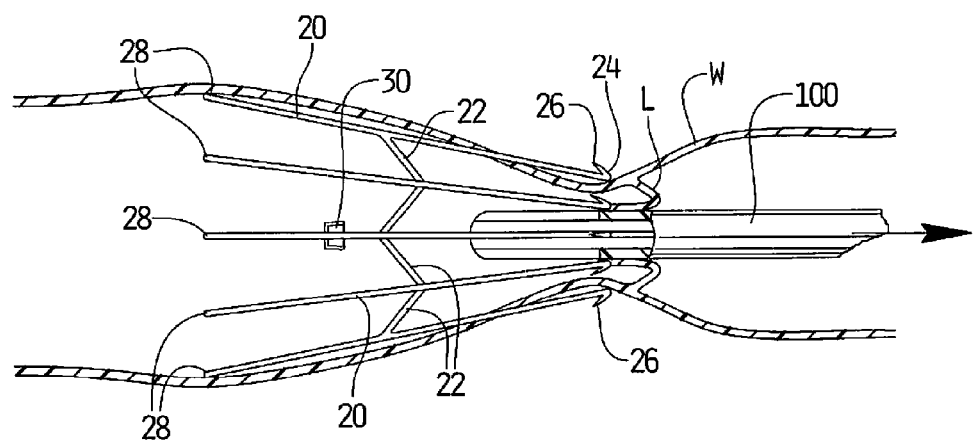
FIG_6
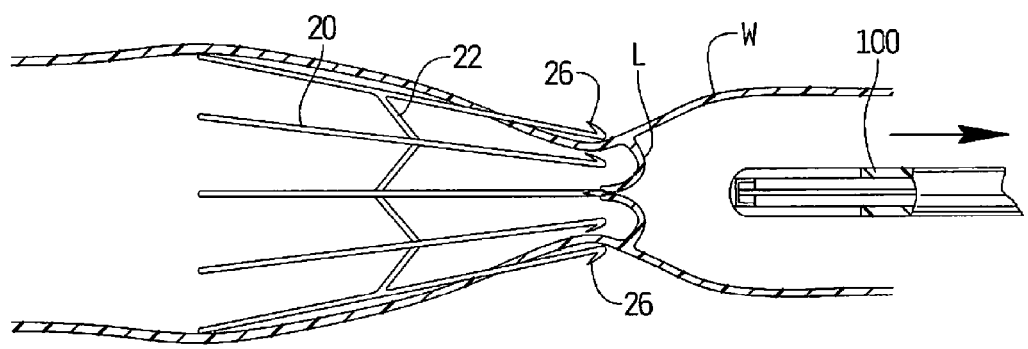
FIG_7

VASCULAR DEVICE AND METHOD FOR VALVE LEAFLET APPOSITION

This application is a divisional of patent application Ser. No. 13/783,246, filed Mar. 2, 2013, which claims priority from provisional application Ser. No. 61/638,643, filed Apr. 26, 2012. The entire contents of each of these applications are incorporated herein by reference.

BACKGROUND

Technical Field

This application relates to a vascular device and more particularly to a vascular device for approximating vein valve leaflets for treating venous valve insufficiency.

Background of Related Art

Veins in the body transport blood to the heart and arteries carry blood away from the heart. The veins have one-way valve structures in the form of leaflets disposed annularly along the inside wall of the vein which open to permit blood flow toward the heart and close to prevent back flow. That is, when blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to prevent blood flow in the opposite, i.e. retrograde, direction after the pressure is relieved. The leaflet structures, when functioning properly, extend radially inwardly toward one another such that the tips contact each other to block backflow of blood.

In the condition of venous valve insufficiency, the valve leaflets do not function properly as they thicken and lose flexibility, resulting in their inability to extend sufficiently radially inwardly to enable their tips to come into sufficient contact with each other to prevent retrograde blood flow. The retrograde blood flow causes the buildup of hydrostatic pressure on the residual valves and the weight of the blood dilates the wall of the vessel. Such retrograde blood flow, commonly referred to as reflux, leads to swelling and varicose veins, causing great discomfort and pain to the patient. Such retrograde blood flow, if left untreated can also cause venous stasis ulcers of the skin and subcutaneous tissue. There are generally two types of venous valve insufficiency: primary and secondary. Primary venous valve insufficiency is typically a condition from birth, where the vein is simply too large in relation to the leaflets so that the leaflets cannot come into adequate contact to prevent backflow. More common is secondary venous valve insufficiency which is caused by clots which gel and scar, thereby changing the configuration of the leaflets, i.e., thickening the leaflets creating a "stub-like" configuration. Venous valve insufficiency can occur in the superficial venous system, such as the saphenous veins in the leg, or in the deep venous system, such as the femoral and popliteal veins extending along the back of the knee to the groin.

A common method of treatment of venous valve insufficiency is placement of an elastic stocking around the patient's leg to apply external pressure to the vein, forcing the walls radially inwardly to force the leaflets into apposition. Although sometimes successful, the tight stocking is quite uncomfortable, especially in warm weather, as the stocking must be constantly worn to keep the leaflets in apposition. The elastic stocking also affects the patient's physical appearance, thereby potentially having an adverse psychological affect. This physical and/or psychological discomfort sometimes results in the patient removing the stocking, thereby preventing adequate treatment.

Another method of treatment has been developed to avoid the discomfort of the stocking. This method involves major surgery requiring the implantation of a cuff internally of the body, directly around the vein. This surgery requires a large incision, resulting in a long patient recovery time, scarring and carries the risks, e.g. anesthesia, inherent with surgery.

Another invasive method of surgery involves selective repairing of the valve leaflets, referred to as valvuloplasty. In one method, sutures are utilized to bring the free edges of the valve cusp into contact. This procedure is complicated and has the same disadvantages of the major surgery described above.

It would therefore be advantageous to provide a method and device to minimally invasively treat venous valve insufficiency without requiring an outer stocking or internal cuff. Such device would thereby avoid the physical and psychological discomfort of an external stocking as well as avoid the risk, complexity and expense of surgically implanted cuffs. Such device would advantageously be inserted minimally invasively, i.e., intravascularly, and function to effectively bring the valve leaflets into apposition.

Commonly assigned U.S. Pat. Nos. 6,695,878 and 6,527,800, the entire contents of which are incorporated herein by reference, disclose an advantageous method and device to minimally invasively treat venous valve insufficiency without requiring an outer stocking or internal cuff. Such device avoids the physical and psychological discomfort of an external stocking as well as avoids the risk, complexity and expense of surgically implanted cuffs. The device is advantageously inserted minimally invasively, i.e., intravascularly, and functions to effectively bring the valve leaflets into apposition. This device first expands against the vessel wall to grasp the wall, and then contracts to bring the vessel wall radially inwardly so the leaflets can be pulled closer together to a functional position.

The vascular devices of commonly assigned U.S. Pat. No. 6,676,698 and Patent Publication No. 2009/0062901, the entire contents of which are incorporated by reference herein, utilizes the device of these foregoing applications for bringing the vessel wall radially inwardly to correct the dilation of the wall, but rather than rely on the patient's existing valve leaflets which may be scarred or non-functional, contain a replacement valve as a substitute for the patient's leaflets. Thus, advantageously, venous valve insufficiency can be treated minimally invasively by bringing the vessel wall inwardly and replacing the patient's valve.

It would be beneficial to further minimize the dimension of a minimally invasive vascular device for approximating valve leaflets to facilitate insertion of the device, and would also be beneficial to reduce the complexity of the device.

SUMMARY

The present disclosure provides an intravascular device which brings the vessel wall adjacent the vein valve radially inwardly to bring valve leaflets into apposition. In one aspect, a vascular device is provided comprising a longitudinal axis and a plurality of struts having a distal portion and a proximal portion. The distal portion of the struts are retained in a converged position, the struts diverging radially outwardly proximally in the converged position. A plurality of vessel engaging members extend from the proximal portion of the struts for engaging the internal wall of the vessel, wherein release of retention of the distal portions of the struts causes the distal portions of the struts to move outwardly away from the longitudinal axis and the proximal portions of the struts to move inwardly toward the longitudinal axis such that the vessel engaging members pull the internal wall of the vessel radially inwardly.

In some embodiments, the device is composed of shape memory material and release of the retention member enables the struts to return to their shape memorized position.

In some embodiments, the device is substantially conical when the distal portions of the struts are retained in the converged position.

In some embodiments, the device includes a retention member which is moved in a distal direction to release the distal portions of the struts.

The device can have connecting struts in an intermediate region of the struts.

In some embodiments, the device is substantially oval in transverse cross-section to form a shorter dimension and a longer dimension, with the longer dimension preferably substantially in line with the valve commissure.

The vessel engaging members can have sharp ends angled outwardly and distally. The device in some embodiments is formed from a tube and the struts are formed from cutouts in the tube.

In accordance with another aspect of the present disclosure, a vascular device is provided comprising a tubular-like member having proximal, intermediate and distal portions, the tubular like member being expandable from a collapsed configuration to an expanded configuration. A plurality of vessel engaging members with penetrating tips extend from the proximal portion, wherein expansion of the member to the expanded configuration causes the proximal portions to move outwardly to penetrate the vessel wall, and subsequent release of the distal portions moves the vessel engaging members radially inwardly to move the vessel wall inwardly.

In some embodiments, the tubular-like member includes a plurality of longitudinal struts and connecting struts interconnecting adjacent longitudinal struts. The device preferably includes a retention member retaining the distal portions of the tubular like member in a converged position, the retention member releasable to release the distal portions to enable movement of the distal portions radially outwardly to a spread position. In some embodiments, the device is substantially oval in cross-sectional dimension.

In accordance with another aspect of the present disclosure, a method for treating venous valve insufficiency is provided comprising the steps of:
  inserting a delivery device and a vascular device having a plurality of legs into a target vessel adjacent valve leaflets of the vessel;
  deploying the vascular device from the delivery device to move a proximal portion of the legs radially outwardly to engage the vessel wall; and
  releasing the distal portion of the legs to enable the proximal portion of the legs to move radially inwardly to move the vessel wall radially inwardly and bring the valve leaflets closer together.

The method can further include the step of moving a retention member of the vascular device axially to release a distal portion of the legs. In some embodiments, the step of releasing the distal portion of the legs enables the vascular device to return to a shape memorized position. The method can further include the step of pulling the retention member proximally to move the legs proximally into contact with the delivery device so that the delivery device cams the legs further outwardly.

Preferably, in the expanded deployed position, the vessel engaging portions of the vascular device are closer to a center longitudinal axis of the device than the distal portions of the device.

In some embodiments, the step of deploying the vascular device to deploy it to an enlarged diameter moves a plurality of penetrating tips of vessel engaging members extending from the proximal portions of the vascular device to penetrate the internal wall of the vessel.

In some embodiments, the delivery device is inserted to a position upstream of the valve leaflets to deliver the vascular device upstream of the valve leaflets; in other embodiments, the delivery device is inserted to a position downstream of the valve leaflets to deliver the vascular device downstream of the valve leaflets.

In some embodiments, the delivery device is inserted through the jugular vein into the popliteal vein or the saphenous vein.

In some embodiments, the vascular device is inserted through the saphenous vein or the popliteal vein to a position downstream of the valve leaflets; in other embodiments, the vascular device is inserted through the saphenous vein or the popliteal vein to a position upstream of the valve leaflets.

BRIEF DESCRIPTION OF THE DRAWINGS

Preferred embodiment(s) of the present disclosure are described herein with reference to the drawings wherein:

FIG. 1 is a perspective view of the vascular device of the present disclosure shown in the fully deployed configuration;

FIG. 2 is a side view of the vascular device of FIG. 1 in the collapsed configuration being delivered into the vessel;

FIG. 3 is a side view similar to FIG. 2 showing the vascular device released from the delivery catheter and in the first expanded configuration;

FIG. 4 is a perspective view of the vascular device in the first expanded position of FIG. 3;

FIG. 4A is a side view similar to FIG. 3 showing the vascular device in a further expanded position to penetrate the vessel wall;

FIG. 5 is a side view similar to FIG. 4A showing release of the retention member to enable expansion of the distal end of the vascular device;

FIG. 6 is a side view similar to FIG. 5 showing movement of the vascular device to the second expanded position wherein the valve leaflets are moved radially inwardly; and FIG. 7 is a side view showing the vascular device approximating the valve leaflets and further showing withdrawal of the delivery catheter.

DETAILED DESCRIPTION OF PREFERRED EMBODIMENTS

Referring now in detail to the drawings where like reference numerals identify similar or like components throughout the several views, FIGS. 1-7 illustrate the vascular device of the present disclosure. The device, designated generally by reference numeral 10, has a proximal (upstream) portion 12 and a distal (downstream) portion 14. The proximal portion 12 is initially expanded radially outwardly to engage the internal wall of the vessel and then subsequently moved radially inwardly to pull the vessel wall radially inwardly as the distal portion 14 is expanded radially outwardly. As the vessel wall is moved radially inwardly, the valve leaflets within the vessel are pulled closer together to a functional condition as shown in the final position of FIG. 7.

FIGS. 1, 6 and 7 illustrate vascular device 10 in the fully deployed or fully expanded configuration to achieve valve apposition and FIG. 2 illustrates vascular device 10 in the collapsed configuration for delivery to the vessel. Intermediate positions of the vascular device 10, e.g., the first expanded configuration and second expanded configuration is shown in FIGS. 3 and 4A, respectively.

Vascular device 10 is preferably composed of a shape memory material, such as a nickel-titanium alloy commonly known as Nitinol, so that in its memorized configuration it assumes the shape shown in FIG. 1. This shape memory material characteristically exhibits rigidity in the austenitic state and more flexibility in the martensitic state. To facilitate passage from the delivery catheter, the shape memory device can be maintained in a collapsed configuration inside a delivery sheath or catheter as described in more detail below. It can be maintained in this position by the delivery catheter wherein upon release, it is no longer constrained by the catheter and moves to the memorized expanded position. Alternatively, the device can be cooled by a saline solution within the delivery catheter to maintain the device below its transition temperature. The cold saline would maintain the temperature dependent device in a relatively softer condition as it is in the martensitic state within the sheath. This facilitates the exit of device 10 from the delivery sheath as frictional contact between the device and the inner wall of the sheath would otherwise occur if the device was maintained in a rigid, i.e., austenitic, condition. When the device 10 is released from the sheath to the target site, it is warmed by body temperature, thereby transitioning in response to this change in temperature to an austenitic expanded condition.

In an alternate embodiment, the device is formed of stainless steel. Other materials are also contemplated.

Device 10 is preferably formed from a tubular member, preferably by laser cutting a tube, although other methods could be utilized. With reference to FIG. 1, device 10, as noted above, includes a proximal portion 12 and a distal portion 14. An intermediate portion 16 is located between the proximal portion 12 and the distal portion 14. Proximal and distal, for convenience, are labeled in the direction of blood flow, with blood flowing in a proximal to distal direction. In the expanded condition, both the proximal and distal portions are expanded away from a central longitudinal axis of the device.

Vascular device 10 includes six struts or legs 20, although a fewer or greater number of struts (legs) could be provided. As shown in FIG. 1, in the fully expanded (deployed) configuration, the struts 20 angle inwardly in a proximal direction such that the distal portions of the struts are further from a central longitudinal axis of the device 10 than the proximal portions of the struts 12. Stated another way, in this fully deployed placement position, the transverse dimension of the distal portion of the device 10 is greater than the transverse dimension of the proximal portion. The adjacent struts 20 are connected by a connecting strut 22. Each connecting strut 22 is angled from a first strut to a second adjacent strut as shown. Thus, if six struts 20 are provided, six connecting struts 22 can also be provided. A different number of struts 20 and connecting struts 22 are also contemplated. Although six longitudinal struts and six vessel engaging members are shown at the end, it should be appreciated that fewer or greater number of struts and vessel engaging members can be utilized. Moreover, not all of the longitudinal struts need to terminate in vessel engaging members provided a sufficient number of struts have vessel engaging members to adequately secure the vessel.

The device 10 is preferably laser cut from a cylindrical tube, forming a series, e.g. six, of symmetrical longitudinal strips or struts 20 terminating at opposite ends in vessel engaging members 24. Thus, the struts 20, 22 are preferably integrally (monolithically) formed from cutouts in a tube so the term connecting strut when used herein includes extending integrally (monolithically) from a portion of the device. However, the device in alternate embodiments is not integrally formed and in this instance, the term connecting struts include separate components fastened or joined (attached) together such as by welding or other methods.

The struts in the first expanded position, as shown in FIG. 3, preferably form a substantially conical shape with the proximal portions of the struts further from the central longitudinal axis of the struts than the distal portions of the struts. In other words, in this first expanded position, the transverse dimension of the distal portion 14 of the device 10 is less than the transverse dimension of the proximal portion 12. In one embodiment, the transverse configuration has a long dimension and a shorter dimension, e.g., an oval. In such configurations, preferably the long dimension would be substantially in line (or substantially parallel) with the valve commissure. Note a line passing through the valve commissure where the leaflets attach to the vessel wall is substantially parallel to a transverse line passing through the site where the valve leaflets meet.

The struts 20 terminate at their proximal ends in vessel engaging members, e.g., hooks 24. These hooks 24 have vessel penetrating tips 26, extending outwardly and partially toward the distal portion 14 of the device 10. When the struts 20 are expanded when released from the delivery catheter as described in more detail below, the hooks 24 engage and penetrate (pierce) the vessel wall to grasp the vessel wall. The sharp penetrating tips 26 penetrate the vessel wall in a radial direction and hold the vessel against axial movement with respect to the device 10. Barbs can be provided on the hooks 24 to restrict radial movement of the vessel with respect to the device 10, thereby together securely retaining (grasping) the vessel wall for radial inward movement described below.

When the distal portion of the device 10 is subsequently expanded, the proximal portions 12 of the struts 20 pivot toward the central longitudinal axis of device 10 to move the vessel wall W radially inwardly to bring the valve leaflets L into apposition as described in more detail below in conjunction with the method of use.

The distal portions of the struts 20 preferably terminate in blunt distal ends 28. These ends 28 are held together during delivery by a retention member, e.g., a retaining cap 30. The retaining cap 30 can be attached to the device 10. Alternatively, the cap can be part of the delivery device. Thus, when retaining cap 30 holds the distal ends 28 of the struts 20 in a converged relationship, the proximal ends of struts 20 can expand radially outwardly as shown in FIGS. 3 and 4. In this memorized first expanded configuration, the transverse cross-sectional dimension of the proximal portion 12 is greater than the internal diameter of the vessel wall W so that the hooks 26 can penetrate the vessel wall. It is also contemplated that alternatively, in the first expanded configuration, the hooks do not penetrate the vessel wall, but require camming of the struts by the delivery catheter. In either case, due to the retention member, the complete memorized position is not achieved at this first stage. When the retaining cap 30 is released as described below, the distal ends 28 of struts 12 move radially outwardly away from the central longitudinal axis of device 10, causing the proximal ends of struts 20 to pivot inwardly toward the central longitudinal axis as shown in FIG. 6.

More specifically, the structure of the vascular device 10 is shown in its first expanded configuration in FIG. 3. Vascular device 10 is composed of a shape memory material, such as Nitinol, so that in its memorized configuration it first assumes the shape shown in FIG. 3 because the distal ends 28 are retained by cap 30. Upon expansion to the first expanded position, the vessel engaging members 20 extend at an angle to the longitudinal axis of the vascular device 10 to enable the vessel engaging members 24 to engage and secure the vessel wall W. This expansion can move penetrating hooks 26 into piercing engagement with the vessel wall W. Alternatively, the initial expansion into the first expanded position can result in movement of the vessel engaging hook 20 into abutment (contact) with or adjacent the vessel wall W, but not yet fully penetrating (see e.g. FIG. 3), and then the struts 20 can be cammed further radially by the distal end of the delivery catheter 100 to penetrate the vessel wall W as shown in. FIG. 4A. When the cap 30 is released, vascular device 10 assumes the shape memorized second memorized position of FIG. 7 (and FIG. 1) as the distal ends 28 of struts 20, no longer restrained, are allowed to move radially outwardly away from the longitudinal axis of the device 10.

There are several different methods of insertion of the vascular device of the present invention for treating venous valve insufficiency of the popliteal or saphenous vein as there are various access vessels for the delivery devices to reach these veins. For example, the delivery catheter 100 can be placed into the popliteal vein in the patient's leg and advanced to a region adjacent the leaflets "L" to deploy the vascular device upstream of the leaflets. The delivery catheter 100 is thus delivered in an antegrade fashion, with the distal tip of the delivery catheter 100 extending upstream of leaflets "L" to deploy the device just upstream (defined in reference to the direction of blood flow) of the leaflets. It alternatively can be further advanced in this antegrade fashion downstream of the leaflets to deploy the device just downstream of the leaflets.

In another approach, the delivery catheter 100 is inserted through the right jugular vein where it will be advanced through the superior and inferior vena cava, past the iliac vein, through the femoral vein, and into the popliteal vein, through leaflets "L" in a retrograde fashion, i.e., opposite the direction of blood flow. The delivery catheter 100 would thus extend through the leaflet region just upstream of the leaflets. Alternatively, the delivery catheter 100 can be advanced up to a region adjacent the leaflets (without passing through the leaflets) to deploy the device just downstream of the leaflets. The delivery catheter 100 can in another approach be placed in the right femoral vein, where it will be advanced in a retrograde manner to the popliteal vein.

In a contralateral approach, the delivery catheter 100 is inserted through the left femoral vein where it will be advanced around the iliac vein and through the right femoral vein into the popliteal vein.

The delivery catheter 100 can have tubing with a stopcock to control saline infusion through the catheter to maintain the vascular device 10 in the cooled martensitic collapsed configuration for delivery. A guidewire port enables insertion of a conventional guidewire (not shown) to guide the delivery catheter intravascularly to the target site. A conventional access or introducer sheath (not shown) would be inserted through the skin and into the access vessel, and the delivery catheter would be inserted into the access vessel through the introducer sheath.

FIGS. 2-7 illustrate the method steps of insertion of the vascular device 10 in an antegrade fashion intravascularly in the popliteal vein "P". The catheter or delivery sheath 100 is inserted over a conventional guidewire (not shown) so the distal tip 112 of the catheter shaft extends past, i.e. downstream, of the valve leaflets L extending annularly from vessel wall "W" as shown in FIG. 2. As can be appreciated, since there is a gap between the valve leaflets L, the valve cannot function properly because the leaflets cannot properly close to prevent backflow. Also, due to the malfunctioning of the valve, the vessel wall can become dilated (not shown) as the weight and pressure of the backflow blood pushes out the vessel wall.

Once the position of the delivery catheter 100 is confirmed by venography, intravascular ultrasound, or other means, the catheter 100 is withdrawn in the direction of the arrow of FIG. 3, exposing the vascular device 10. (Alternatively, a pusher can advance the device 10 from the catheter 100). When the catheter 100 has been fully withdrawn to expose the device 10, the device 10 transitions to its austenitic phase and the first memorized expanded configuration of FIG. 4A. The retaining cap 30 maintains the distal portion 28 of the struts 20 in the converged position. In an alternate embodiment, the first memorized expanded position is that of FIG. 3, wherein the struts require a further camming action to move the hooks 24 into the vessel wall to the position of FIG. 4A.

In this first expanded position, vessel engaging members 24 penetrate the vessel wall (FIG. 4A), or in an alternate embodiment, move adjacent the vessel wall and into contact with, for subsequent penetration into the vessel wall W. In this latter embodiment, the device 10 can then be pulled proximally or the catheter 100 moved distally so that an inner surface of the struts 20, adjacent the converging region, engage the edge 112 of the catheter 100 to be cammed further radially outwardly so that the sharp tips 26 penetrate the vessel wall to firmly grasp and secure it as shown in FIG. 4A. The securement to the vessel wall restricts both radial and axial movement of the vessel to enhance retention by the device 10. In the first expanded position and in the second expanded position (if applicable), the transverse dimension at the proximal portion 12 of the device 10 exceeds the transverse dimension at the distal portion 14.

After retention of the vessel wall as in FIG. 4A, the cap 30 is moved distally by distal movement of pusher rod 35, to release the distal ends 8 of the struts 20 from the cap 30 as shown in FIG. 5. This causes the distal portions 16 of struts 12 to diverge radially outwardly away from the central longitudinal axis, causing the proximal portions of the struts 20 to pivot inwardly toward the central longitudinal axis, thereby moving the penetrating tips 26 and the attached vessel wall inwardly as shown in FIG. 6. That is, as the struts 20 are pivoted, due to the engagement of the vessel engaging members 24 with the internal wall of the vessel, the vessel wall is pulled radially inwardly, thereby pulling the leaflets radially inwardly to the position of FIG. 7 to close the gap between the leaflets L. As can be appreciated, the vessel wall is no longer dilated and the valve leaflets are sufficiently approximated such that their tips contact to block backflow and their function is therefore restored. The device 10 remains inside the vessel, maintaining the approximation of the vessel wall to maintain the proper functioning of the leaflets.

In an alternate method of placement of the vascular device, the vascular device 10 is placed upstream (with respect to the direction of blood flow) of the valve leaflets. The delivery catheter is inserted in the same antegrade manner as described above, except it is advanced proximal of the valve leaflets L to enable upstream delivery of the device 10. Thus, the device 10 would grasp the vessel wall upstream of the valve leaflets to pull the vessel wall radially inwardly to bring the leaflets into apposition.

As noted above, for retrograde insertion of the vascular device 10, the delivery catheter, e.g. catheter 100, is inserted in a direction against the blood flow so tip 110 extends past the valve leaflets "L" in the popliteal vein and the catheter 100 is positioned so the device 10 will be deployed upstream of the leaflets. The device can also alternatively be delivered in a retrograde fashion and deployed upstream of the leaflets if the tip 110 is placed upstream of the leaflets.

The vascular device 10 could also include a valve attached thereto to replace the valve leaflets L. Thus, the dilated vessel wall is pulled radially inwardly in the manner described above, except that instead of relying on the leaflets L, the valve of the vascular device would function to open and close to respectively allow and block blood flow.

While the above description contains many specifics, those specifics should not be construed as limitations on the scope of the disclosure, but merely as exemplifications of preferred embodiments thereof. For example, instead of moving the catheter to expose the vascular device, the device can be advanced with respect to the catheter or both the catheter and device can move relative to each other in opposite directions. Those skilled in the art will envision many other possible variations that are within the scope and spirit of the disclosure as defined by the claims appended hereto.

What is claimed is:

1. A method for treating venous valve insufficiency comprising the steps of:
    inserting a delivery device and a vascular device having a plurality of legs into a target vessel adjacent valve leaflets of the vessel;
    deploying the vascular device from the delivery device to move a proximal portion of the legs radially outwardly to engage a wall of the vessel; and
    subsequently releasing a distal portion of the legs to move the proximal portion of the legs radially inwardly to move the vessel wall radially inwardly and bring the valve leaflets closer together;
    wherein the proximal portion of the legs have vessel penetrating members, and wherein in an expanded placement position of the vascular device, the vessel penetrating members are spaced from a center longitudinal axis of the vascular device a radial distance less than a radial distance distal portions of the legs are spaced from the center longitudinal axis; and
    prior to releasing the distal portion of the legs, the vessel penetrating members are spaced from the center longitudinal axis a radial distance greater than a radial distance distal tips of the legs are spaced from the center longitudinal axis.

2. The method of claim 1, wherein the step of releasing the distal portion of the legs includes moving a retention member of the vascular device axially, the retention member deployable from the delivery device.

3. The method of claim 1, wherein the step of releasing the distal portion of the legs enables the vascular device to return to a shape memorized position.

4. The method of claim 1, further comprising the step of pulling a retention member proximally to move the legs proximally into contact with the delivery device, the delivery device camming the legs further outwardly.

5. The method of claim 1, wherein the delivery device is inserted to a position upstream of the valve leaflets to deliver the vascular device upstream of the valve leaflets.

6. The method of claim 1, wherein the delivery device is inserted to a position downstream of the valve leaflets to deliver the vascular device downstream of the valve leaflets.

7. The method of claim 1, wherein the vascular device is inserted through the saphenous vein or the popliteal vein to a position downstream of the valve leaflets.

8. The method of claim 1, wherein the vascular device is inserted through the saphenous vein or the popliteal vein to a position upstream of the valve leaflets.

9. The method of claim 1, wherein the device is substantially conical in configuration.

10. The method of claim 1, wherein the device is substantially oval in transverse cross-section to form a shorter dimension and a longer dimension and the longer dimension is substantially parallel with a valve commissure.

11. The method of claim 1, wherein the device is formed from a tube and the struts are formed from cutouts in the tube.

12. The method of claim 1, wherein the device includes a retention member retaining the distal portion of the legs and the step of releasing a distal portion of the legs includes the step of releasing the retention member into the vessel.

13. The method of claim 1, wherein the device has free ends at the proximal portion and distal portion.

14. The method of claim 1, wherein release of the legs causes distal tips of the legs to diverge radially outwardly.

15. A method for treating venous valve insufficiency comprising the steps of:
    inserting a delivery device and a vascular device having a plurality of legs into a target vessel adjacent valve leaflets of the vessel;
    deploying the vascular device from the delivery device to move a proximal portion of the legs radially outwardly to engage a wall of the vessel; and
    subsequently releasing a distal portion of the legs to move the proximal portion of the legs radially inwardly to move the vessel wall radially inwardly and bring the valve leaflets closer together, wherein the step of releasing the distal portion of the legs releases the legs from a converged position, the proximal portion of the legs are normally angled inwardly as the distal portion of the legs are normally angled outwardly.

16. The method of claim 15, wherein release of the legs causes distal tips of the legs to diverge radially outwardly.

17. The method of claim 16, wherein the device has free ends at the proximal portion and distal portion.

18. A method for treating venous valve insufficiency comprising the steps of:
    inserting a delivery device and a vascular device having a plurality of legs into a target vessel adjacent valve leaflets of the vessel;
    deploying the vascular device from the delivery device to move a proximal portion of the legs radially outwardly to engage a wall of the vessel;
    subsequently releasing a distal portion of the legs to move the proximal portion of the legs radially inwardly to move the vessel wall radially inwardly and bring the valve leaflets closer together, wherein the step of releasing the distal portion of the legs includes moving a retention member of the vascular device axially, wherein the retention member is distal of the proximal portion of the legs and remains distal during release of the distal portion of the legs.

\* \* \* \* \*